United States Patent [19]

Maeda

[11] 4,430,192

[45] Feb. 7, 1984

[54] OXYGEN GAS ANALYZER USING SOLID ELECTROLYTE

[75] Inventor: Masato Maeda, Tokyo, Japan

[73] Assignee: Yokogawa Hokushin Electric Corporation, Tokyo, Japan

[21] Appl. No.: 353,920

[22] Filed: Mar. 2, 1982

[30] Foreign Application Priority Data

May 26, 1981 [JP] Japan .............................. 56-79865
Mar. 6, 1981 [JP] Japan ............................. 56-31125[U]

[51] Int. Cl.³ .......................................... G01N 27/58
[52] U.S. Cl. ................................. 204/410; 204/427; 204/428
[58] Field of Search ............... 204/195 S, 1 S, 410, 204/427, 428; 422/98

[56] References Cited

U.S. PATENT DOCUMENTS

| 3,915,828 | 10/1975 | Cleary et al. | 204/195 S |
| 4,076,608 | 2/1978 | Fujishiro et al. | 204/195 S |
| 4,247,380 | 1/1981 | McIntyre | 204/195 S |
| 4,284,487 | 8/1981 | Barnes et al. | 204/195 S |
| 4,339,318 | 7/1982 | Tanaka et al. | 204/195 S |

Primary Examiner—G. L. Kaplan
Attorney, Agent, or Firm—Moonray Kojima

[57] ABSTRACT

An oxygen meter for measuring the oxygen concentration in a measured gas, having a probe type detecting section carrying at its end a solid electrolyte unit constituting a partition wall, so as to produce a signal corresponding to the difference in the oxygen concentration between the inner side and the outer side of the partition wall. The oxygen meter is adapted to be exposed to the flow of the gas to be measured or into a furnace through a hole formed in the furnace wall, thereby to continuously produce a signal representing the oxygen concentration in the gas to be measured.

6 Claims, 13 Drawing Figures

OXYGEN GAS ANALYZER USING SOLID ELECTROLYTE

BACKGROUND OF THE INVENTION

1. Field of the Invention.

This invention relates to a solid type oxygen meter, and more particularly, to such an oxygen meter having a probe type detector adapted to produce a signal representing the difference in oxygen concentration between the inner side and the outer side of a partition wall formed by a solid electrolyte supported on the end of the probe type detector.

2. Description of the Prior Art.

Figure 1:
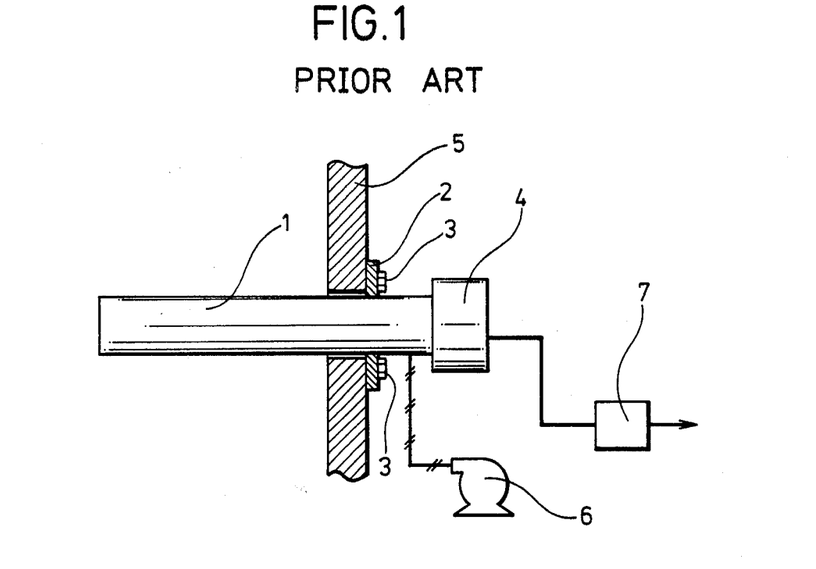
FIG. 1 depicts a diagramtic view of a conventional oxygen meter.

FIG. 1 shows a typical known oxygen meter of direct insertion type. This oxygen meter has a probe 1 having an end adapted to be inserted into a stack or a furnace with a flange 2 thereof fastened to the furnace or stack wall 5 by means of bolts 3. The probe is provided at its end with a solid electrolyte such as zirconium, bismuth oxide or the like; detecting electrodes disposed across the solid electrolyte; temperature sensor; heater; etc. The oxygen meter further has a terminal box 4 through which the detecting electrodes, temperature sensor and heater are connected to external circuits. The oxygen meter also has a signal receiving portion 7 adapted to produce a signal corresponding to the oxygen concentration. The signal receiving portion 7 has a linearizing section for linearizing the detection signal and a temperature adjusting section employing a heater as a contro means. The oxygen meter is also provided with a pump 6 adapted to forcibly supply air as a reference gas into probe 1.

Thus, the conventional oxygen meter requires a pump for supplying probe 1 with a reference gas (air) and accordingly, the cost of production is raised uneconomically. In addition, the realiability of operation is lowered due to the employment of moving parts, such as the pump.

As an alternative, it has been proposed to adapt such an oxygen meter to introduce instrumentation air into probe 1. This system, however, requires a specific piping work and therefore, is not preferred from an economical point of view.

Figure 2:
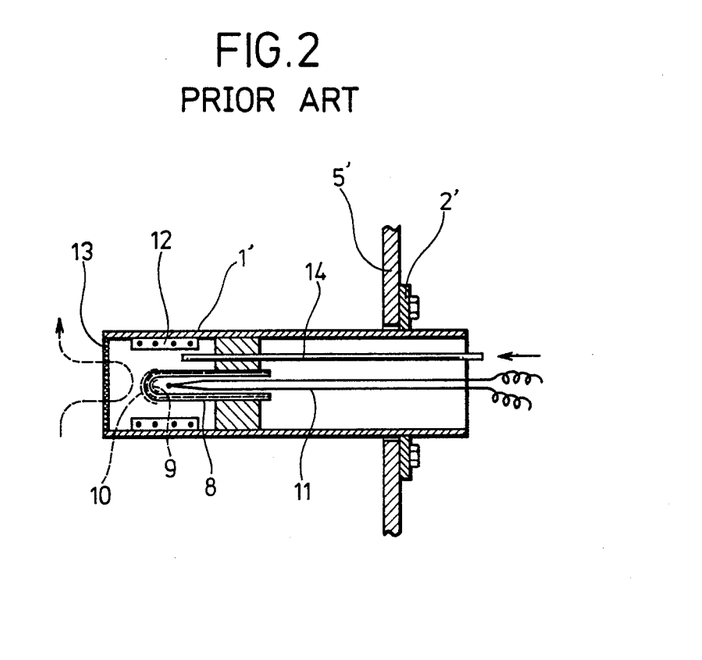
FIG. 2 depicts an elevational cross-sectional view of the detecting section of a conventional oxygen meter, such as depicted in FIG. 1.

FIG. 2 illustrates the construction of the detecting section of the conventional oxygen meter of the kind described in FIG. 1. A probe 1' has a flange 2' adapted to be secured, for example by bolts (unnumbered) to a furnace wall or stack wall 5' with its end inserted into the furnace or stack. A test tube type solid electrolyte 8, such as zirconium, bismuth, or the like material is provided within probe 1'. Solid electrolyte 8 is secured to the end of probe 1' with its closed end located at the end of probe 1' so as to form a partition wall separating the end portion of probe 1' from other portions thereof. Electrodes 9 and 10 are closely secured to the inner and outer sides of the wall of solid electrolyte 8. A temperature sensor 11 is adapted to sense the temperature of solid electrolyte 8 which is adapted to be heated by a heater 12. Temperature sensor 11, heater 12 and a temperature adjusting section (not shown), in combination, constitute a temperature control system adapted to maintain solid electrolyte 8 at a substantially constant temperature. In operation, a signal corresponding to the difference of oxygen concentration between the inner and outer side of solid electrolyte 8 is derived from electrodes 9 and 10 through respective leads which are not shown. A filter 13 is provided at the end of probe 1' and is adapted to prevent dust from attaching to the wall surface of solid electrolyte 8. A conduit 14 has one end located at the closed end (outer side) of solid electrolyte 8 and the other end located at the portion opposite to the end of probe 1' so as to enable introduction of a calibration gas into the closed end of solid electrolyte 8.

In this type of oxygen meter, it is necessary to occasionally renew or replace the solid electrolyte 8 in order to maintain the desired precision of measurement. The amount of work required for renewal or replacement, however, is made quite troublesome and time-consuming, because probe 1' is provided with various parts at its end as described.

SUMMARY OF THE INVENTION

Accordingly, an object of the invention is to provide a solid electrolyte type oxygen meter having a replaceable electrolyte unit without any lead wires, which permits easy renewal or replacement of the solid electrolyte in the probe type detector, thereby to reduce the cost of maintenance and thereby overcome the aforementioned deficiencies and disadvantages of the prior art.

To this end, according to the invention, there is provided an oxygen meter comprising a test tube type solid electrolyte unit having a contact portion mounted on the inner wall of a probe adjacent to the end thereof through the medium of an electrically insulating member, a first electrode and a second electrode which are closely secured to the outer surface and the inner surface of the closed end or its vicinity, a first lead closely secured to the outer wall surface and providing an electrical connection between the first electrode and the contact portion and a second lead closely secured to the inner wall surface and providing an electrical connection between the second electrode and the open end surface; and a first conductor and a second conductor which are electrically connected to the contact portion and the open end surface, respectively, thereby to transmit the signals produced by the first and second electrodes.

Another object is to provide a solid electrolyte type oxygen meter wherein, in order to facilitate the renewal or replacement of the solid electrolyte, a cell unit comprising a test tube type electrolyte unit and a flange integral therewith, for example, is inserted with its closed end directed inwardly into the end of the probe and a calibration gas conduit is easily separable from the main body of the oxygen meter.

This object is achieved by a solid electrolyte type oxygen meter comprising a cell unit including a conduit disposed in a probe such that one end of the conduit is disposed near the end of the probe while the other end projects toward the portion of the probe opposite to the end, a test tube solid electrolyte unit and a flange integral with the solid electrolyte, the cell unit being inserted into and secured to the probe with the closed end of the solid electrolyte directed inwardly, a substantially U-shaped pipe having one end inserted into the internal cavity of the solid electrolyte unit while the other end is connected to the portion of the conduit near the end of the probe, and a flange supporting the U-shaped pipe and jointed to the flange of the cell unit, the flange being adapted to be fixed to the end of the probe by means of a fixing tool.

Still another object is to provide an oxygen meter having a less expensive and more reliable means for introducing a reference gas.

This third object is achieved by a solid electrolyte type oxygen meter having a reference gas introduction means including a partition plate which divides the internal space of the probe into two sections in the longitudinal direction thereof, a communicating portion disposed in the vicinity of the solid electrolyte unit and providing a communication between the two sections, and a communicating portion disposed in the portion of the probe opposite to the end or its vicinity and providing communication between the divided sections and the outside atmosphere.

DETAILED DESCRIPTION OF PREFERRED EMBODIMENTS.

Figure 3:
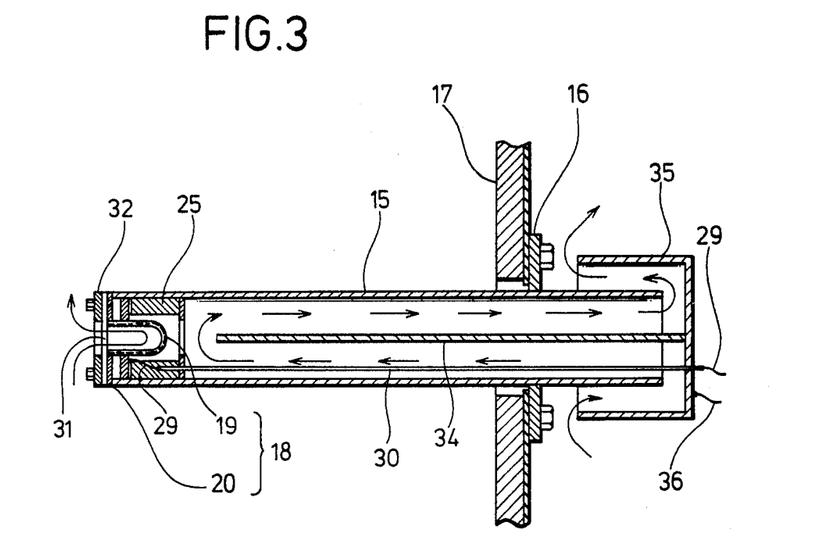
FIG. 3 depicts an elevational cross-sectional view of an illustrative embodiment of the invention.
Figure 4A:
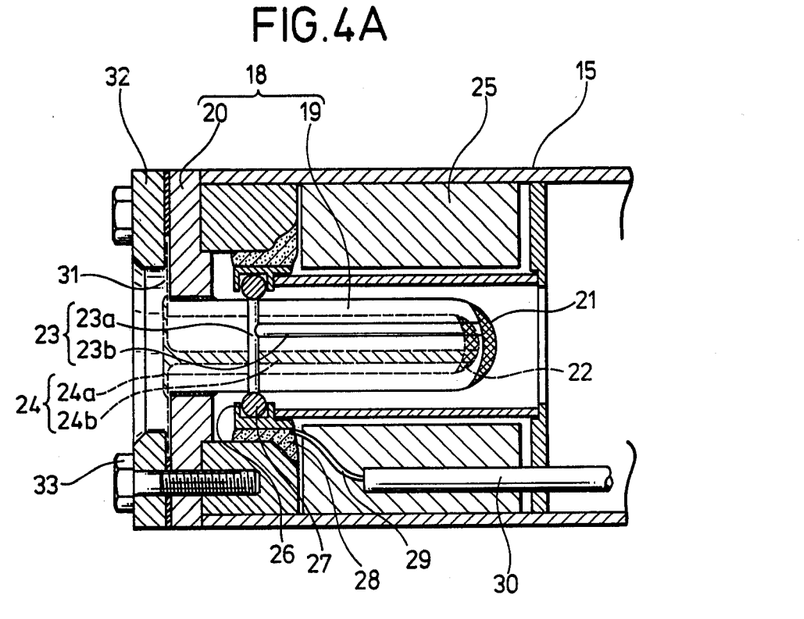
FIGS. 4A and 4B depict enlarged views of portions of the probe type detecting section of the embodiment of FIG. 3.
Figure 4B:
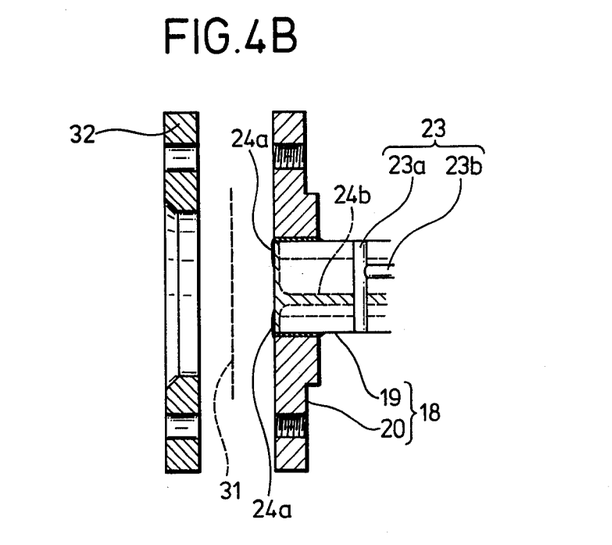

FIG. 3 depicts essential parts of an oxygen meter constructed in accordance with the illustrative embodiment which achieves the aforementioned first object of the invention. FIGS. 4A and 4B depict enlarged view of certain parts of the detecting section of the meter. In these figures, probe 15, made of an electrically conductive material and having a flange 16 welded to a cylindrical barrel like portion thereof, is secured, such as by bolts (not numbered) to a wall 17 of a stack or furnace, by means of flange 16. A cell unit 18 is provided, for easy mounting and demounting, at the end of probe 15, and comprises a test tube shaped solid electrolyte unit 19 (hereinafter called electrolyte unit), comprising, for example, a solid electrolyte such as zirconium; and a flange 20. Advantageously, in accordance with the invention, the electrolyte unit 19 can be readily attached to or detached from the probe and replaced or renewed with a similar unit 19. In this embodiment, the electrolyte unit 19 is disposed together with the flange 20, and together forms a cell unit, which cell unit is easily attached to or detached from the probe.

The solid electrolyte unit 19 includes porous platinum electrode films 21 and 22 (see FIGS. 4A and 4B) provided on the outer wall surface and the inner wall surface of a closed end thereof; a lead 23 comprising a ring shaped portion 23a formed on the outer wall surface of electrolyte unit 19 by baking platinum paste thereof, and a connecting portion 23b through which ring shaped portion 23a is connected to electrode film 21; and a lead 24 comprising a contact surface 24a formed by baking platinum paste on an open end surface of the electrolyte unit 19, and a connecting portion formed on the inner wall surface thereof, and formed by baking platinum paste and used to provide an electrical connection between contact surface 24a and electrode film 22, in the manner depicted.

A heater 25 (See FIG. 3) is provided within probe 15 near the solid electrolyte unit 19, for heating the unit 19. This constitutes, in combination with a temperature sensor (not shown) provided on the closed end of the unit 19 and a temperature controller (not shown), a temperature control system for maintaining the unit 19 at a predetermined constant temperature. A contact ring 26 (see FIG. 4A) is provided with a recessed inner peripheral surface and is affixed to probe 15 by a highly insulative adhesive 28, such as SUMICERAN (a commercially available product). A coil contact 27 is adapted to be fitted in the recess of the contact ring 26 and comprises a nichrome wire or a wire of heat resistant and anti-oxidation metal. A wire lead 29, covered by an insulator 30, is disposed in the probe 15 with one end thereof connected to contact ring 26 with another end thereof connected to an external terminal (not shown).

Coil contact 27 is held in electrical contact with ring shaped portion 23a of lead 23 with electrolyte unit 19 mounted on probe 15, so that an electrical path is formed via electrode film 21, connecting portion 23b, ring portion 23a, coil contact 27, contact ring 26, and wire lead 29. A mesh filter 31 made, for example of stainless steel, is pressed and secured to the open end surface of solid electrolyte unit 19 by means of a flange 32 and bolt 33. An electrical path is formed by electrode film 22, connecting portion 24b, contact surface 24a, mesh filter 31, flange 20, flange 32 and probe 15.

A partition plate 34 (see FIG. 3) is positioned within probe 15 and is adapted to divide the internal cavity of probe 15, other than the portion near the electrolyte unit 19, into an upper section and lower section. A bottom equipped metallic plate 35 is provided at the portion of probe 15 opposite to the end and is made of a conductive material. A lead wire 36 is connected to metal plate 35. Metal plate 35 is so constructed as to permit sections of the internal cavity of probe 15 to communicate with the outside independently of each other. The metal plate 35 is electrically connected to probe 15 so that the electric path, including electrode film 22 and probe 15 is connected to an external terminal (not shown) through wire lead 36. Lead wire 29 is connected electrically to electrode film 21 as above discussed.

In the detecting section of the oxygen meter, the end of probe 15 is held in a stream of hot flue gas, for example, having a temperature of about 200° to 500° C., and forms the measuring means.

The gas to be measured for oxygen content comes into contact with solid electrolyte unit 19 through filter 31 by diffusion and convection to continuously contact the inner surface of the unit 19. The gas contacting the outer wall surface of the electrolyte unit 19 (i.e. the air in probe 15) has been heated to a high temperature of about 700° to 850° C. by heat derived from the measured gas and heat produced by heater 25. Passage of natural convection of air is formed to include the outside atmosphere, lower section of the internal cavity of probe 15, end of probe 15 (near the electrolyte unit 19), upper section of the internal cavity of probe 15 and the outside atmosphere (see arrows in FIG. 3). Thus, the reference gas side of the electrolyte unit 19 is always held in contact with fresh air, so that it is possible to obtain stably a detection signal between the two electrode films 21 and 22. A signal is then derived through wire leads 29 and 30. FIG. 3 shows probe 15 held in a horizontal posture. It has been experimentally confirmed, however, that sufficient convection of air is maintained even if probe 15 is inclined with the end thereof directed downwardly until probe 15 takes a substantially vertical position.

As has been described above, cell unit 18 (comprising electrolyte unit 19 and flange 20) is secured to the end of probe 15 by means of flange 32 and bolts 33, and electrical connections between electrode films 21, 22 and external terminals are made through leads 23 (comprising ring shaped portion 23a and connecting portion 23b) lead 24 (comprising contact surface 24a and connecting portion 24b), coil contact 27 and mesh filter 31, respectively. Thus, it is possible to easily mount and demount cell unit 18 from probe 15 and thereby easily renew or replace the electrolyte unit 19.

Thus, according to the invention, there is provided a solid electrolyte type oxygen meter having a cell unit comprising the electrolyte unit and lacking any lead wires, which cell unit can be easily mounted and demounted and thereby easily replace the electrolyte unit. In this manner, advantageously, the maintenance cost can be readily reduced, and the renewal or replacement of the electrolyte unit can be easily made without any complex equipment or procedures.

Figure 5:
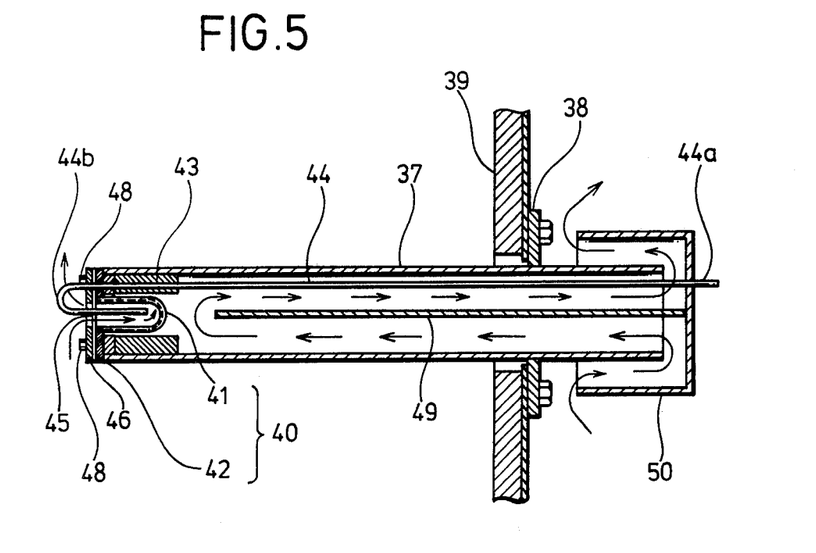
FIG. 5 depicts an elevational cross-sectional view of another illustrative embodiment of the invention.
Figure 6:
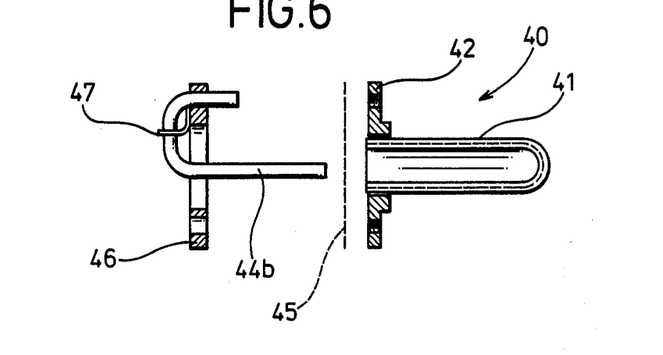
FIG. 6 depicts an enlarged view of disengaged parts of the detecting section of the embodiment of FIG. 5.

FIGS. 5 and 6 show the construction of an oxygen meter constructed in accordance with another illustrative embodiment which fulfills the aforementioned second object of the invention. More specifically, FIG. 5 illustrates essential parts of the detecting section of an oxygen meter, while FIG. 6 depicts an enlarged view of parts thereof. Various lead wires, sensors, etc. are not shown in these figures for clarity of description. The wire connections of FIGS. 3, 4A, 4B are indicative of such wire leads which can be used. In the remaining figures, similar parts have been omitted for clarity of description.

A probe 37 having a flange 38 welded thereto and is mounted on a flue or a furnace wall 39 by means of flange 38 (with bolts not numbered). A cell unit 40, comprising a test tube shaped solid electrolyte unit 41, made for example of zirconium, and a flange 42, is adapted to be readily mounted and demounted on the end of probe 37. A heater 43 is provided with probe 37 and within the area of the electrolyte unit 41, for heating the unit 41. Although not shown, porous electrode films of platinum are formed on both surfaces of the end (bottom of the test tube shaped unit) of solid electrolyte unit 41, as described in FIG. 3.

A signal corresponding to the difference in the oxygen concentration between the two chambers separated by the wall of the unit 41 (i.e. between the inner side and the outer side of the probe 37) is taken out of probe 15 by means of the electrode film and connecting leads. A temperature sensor provided at the end of the electrolyte unit 41 constitutes, in combination with a temperature controller and heater 43, a temperature control system which serves to maintain the unit 41 at a predetermined constant temperature.

A conduit 44, comprising a straight portion 44a and a U-shaped portion 44b is held by a mesh filter 45 provided at the open end of the electrolyte unit 41, with the filter 45 having an attaching flange 46. Flange 46 (see FIG. 6) supports the U-shaped portion 44b of conduit 44, through a bracket 47 (see FIG. 6) and is adapted to be secured to probe 37 by means of bolts 48 (see FIG. 5) thereby to removably attach cell unit 40 to the end of probe 37.

In this state, U-shaped portion 44b of conduit 44 is positioned in the hollow cavity of electrolyte unit 41, while the other end of U-shaped portion is connected to one end of straight portion 44a of conduit 44. Although the conduit does not clearly show a connector between the U-shaped portion and the straight portion a connecting segment is preferable.

A partition plate 49 (see FIG. 5) is positioned in probe 37 and divides the internal cavity thereof, other than in the vicinity of the electrolyte unit 41, into an upper and a lower section. A bottom-equipped cylindrical lid 50 is secured to the portion of probe 37 opposite the end thereof. Lid 50 permits sections of the internal cavity of probe 37 to communicate with the outside atmosphere independently of each other, as depicted.

In operation, the end portion of probe 37 is held in the stream of the hot flue gas to be measured. The flue gas has a temperature of about 200° to 500° C. The gas to be measured comes into electrolyte unit 41 through filter 45 by diffusion and convection, thereby to make continuous contact with the inner wall surface of electrolyte unit 41. On the other hand, the gas contacting the outer wall surface of the electrolyte unit 41 (i.e. the air inside probe 37) is heated to a high temperature of about 700° to 850° C. by heat from the gas to be measured and heat produced by heater 43. Consequently, passage of natural convection of air is formed, to include, as shown by arrows in FIG. 5, the outside atmosphere, lower section of internal cavity of probe 37, end of probe 37 (near electrolyte unit 41), upper section of the internal cavity of probe 37 and the outside atmosphere.

Thus, the reference gas side of the unit 41 is always kept in contact with fresh air, so that a stable signal is derived from the electrodes on the unit 41. In the measuring operation above discussed, the conduit 44 is normally kept closed so that the gas in conduit 44 does not flow. The presence of conduit 44, thus, does not adversely affect at all the state of flow and composition of the measured gas flowing into unit 37. It is, however, possible to improve the response by making use of conduit 44. Namely, the introduction of the measured gas into unit 37 is accelerated to promote substitution of gas, by connecting the end of conduit 44 outside the unit 4, to a suction port of an ejector or the like (not shown).

An explanation will be made as to the calibrating operation and cleaning operation. Calibration is conducted by introducing, through conduit 44 into unit 41, a calibration gas having a pressure somewhat higher than the pressure of the measured gas. Since the calibration gas has a pressure higher than the measured gas, the substitution of two gases in the unit 37 can be made in quite a smooth manner to permit an accurate substitution of two gases.

By using a cleaning gas (e.g. air for measuring instrument) in place of the calibration gas, it is possible to remove any dust which may be attached to the filter 46, and unit 37, by a blowback operation.

For renewing or replacing the electrolyte unit 37, bolts 48 are first loosened to separate the straight portion 44a and the U-shaped portion 44b of conduit 44 from each other, and cell unit 40 comprising unit 41 and flange 42, is withdrawn from the end of probe 37. It is, therefore, possible to renew or replace the solid electrolyte unit 41 in an easy manner.

As has been described, in the solid electrolyte type oxygen meter of the invention, a cell unit 40 comprising a test tube type solid electrolyte unit 41 and a flange 42 integral therewith is inserted into and attached to the end of probe 37 with the closed end of solid electrolyte unit directed inwardly. In addition, conduit 44 for introducing the calibration gas can be separated (i.e. the U-shaped part 44b from the straight portion 44a) at a portion thereof near the end of probe 37. It will be seen that the described arrangement of the oxygen meter remarkably facilitates the protective maintenance work for replacing or renewing the solid electrolyte.

Figure 7:
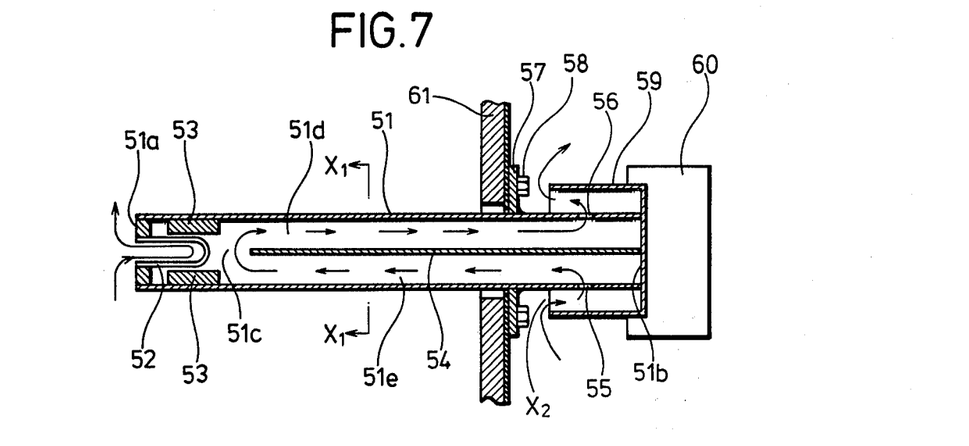
FIG. 7 depicts an elevational cross sectional view of still another illustrative embodiment of the invention.

FIG. 7 shows an oxygen meter constructed in accordance with still another embodiment of the invention which achieves the aforementioned third object of the invention. The oxygen meter includes a probe 51 having a flange 57 welded to the barrel thereof and mounted on a stack or furnace wall 61 by bolts 58, and provided with through holes 55 and 56 formed in the side wall near the portion 51b thereof opposite to the end, a test tube type solid electrolyte unit 52 mounted on the end of probe 51 with flange 51a, a heater 53 for heating the end (bottom of the test tube unit) of the electrolyte unit 52, a partition wall plate 54 within probe 51 adapted to divide the internal cavity of probe 51 into two sections 51d and 51e, while leaving a communicating portion 51c in the vicinity of the end of unit 52, and a bottom equipped cylindrical lid 59 adapted to close end 51b of probe 51, as described. Detecting electrodes formed on both surfaces of the end wall of the unit 52, temperature sensor (not shown) for sensing the temperature at the end portion of the unit 52, and various connecting circuits are not shown for clarity of description. Reference to FIGS. 3, 4A and 4B, will show how these connections may be effected. Terminal box 60 is used for connecting the electrodes, temperature sensors, heaters, etc., to external circuits. A linearizing portion may be employed for linearizing a detection signal derived through terminal box 60 and adapted to deliver the linearized signal as its output. A signal receiving portion may be employed. The detecting end of probe 51 is inserted into the flue to measure the oxygen content of the gas therein, in the same manner as above described. The probe end 51 may be either a flange connected to the unit 52 or be an end unit to which the unit 52 may be readily inserted.

Figure 8A:
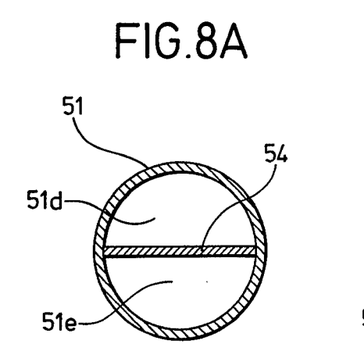
FIG. 8A depicts a sectional view taken along the line $x_1—X_1$ of FIG. 7.

FIG. 8A depicts a cross sectional view along $X_1-1$, in FIG. 7, and shows probe 51 having a partition 54 therein dividing the space therein to section 51d and 52e.

Figure 8B:
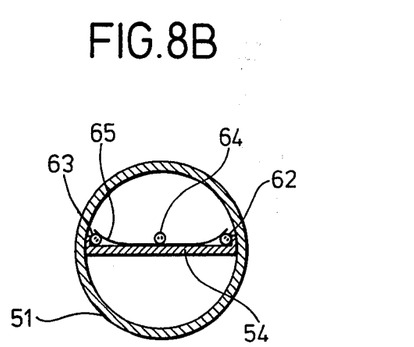
FIG. 8B depicts an arrangement of various lead wires with the probe.

Although not shown in FIG. 7, the wiring to the detecting electrodes, temperature sensor and heater 53 may be arranged by using the partition plate 54, as show in FIG. 8B, as the substrate for mounting same. For example, heater lead wire 62 and electrode leads 63 may be placed on partition plate 54 and pressed and fixed by means of a leaf spring 65. At the same time, a temperature sensor lead 64 may be fixed to the top of spring 65 by spot welding.

The oxygen meter of this embodiment having the above described construction, operates in the following manner. In the measuring state, end 51a of probe 51 is held in the stream of the gas to be measured which has a temperature of about 200° to 500° C. and one (e.g. inner) wall surface of the electrolyte unit 52 is held in continuous contact with this stream of gas to be measured. The space inside probe 51 is communicated with the outside atmosphere through holes 55 and 56, and therefore, is always filled with fresh air. Thus, the detection electrodes provided on both surfaces of the wall of the electrolyte unit 52 produce a detection signal in accordance with the Nernst's equation using the air as reference gas. The detection signal is delivered to a signal receiving portion in terminal unit 60, which conducts a predetermined arithmetic operation to provide a signal corresponding to the oxygen concentration of the measured gas. The air in the probe 51 is heated to a high temperature of about 700° to 850° C. by heat derived from the measured gas and heat produced by the heater 53. Passage of natural convection of air is formed to include the circuit comprising outside atmosphere, through hole 55, section 51e, communicating portion 51c, section 51d, through hole 56 and outside atmosphere as shown by arrows in FIG. 7. Consequently, the other wall (outside) surface of unit 52 is maintained in contact with fresh air serving as the reference gas, so that the oxygen meter provides a stable output signal.

Figure 9:
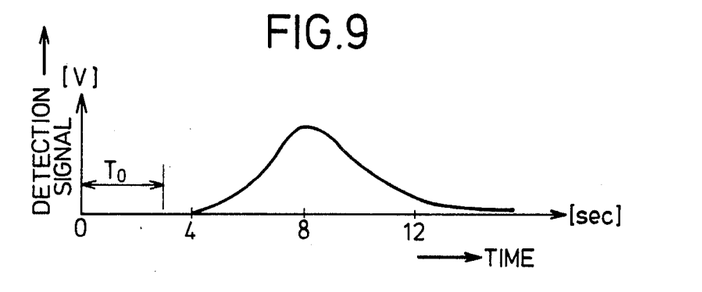
FIG. 9 depicts a graph illustrating the principles of operation of the oxygen meter shown in FIG. 7.

The present inventor has conducted the following test to confirm the presence of the convection of air. Atmosphere was introduced into the area where the measured gas flowed, as shown in FIG. 7, and both sides of the wall of unit 52 were placed under atmosphere of air. The space inside probe 51 was maintained at a high temperature of about 700° C. Then, $N_2$ gas containing about 1% of $O_2$ gas was supplied for 2 to 3 seconds to the area $X_2$ in the vicinity of through hole 55. FIG. 9 is a graph showing the change of the detection signal. The time To represents the time length over which the 1% $O_2$ gas was blown. As will be understood from FIG. 9, the change in the $O_2$ gas concentration appearing at area $X_2$ is transmitted to the end of unit 52 in about 8 seconds. Since the volume of section 51e in probe 51 used in the experiment was about 150 ml, the flow rate of air moved by the convection can roughly be calculated to be about 1125 ml/min.

Figures 10, 11:
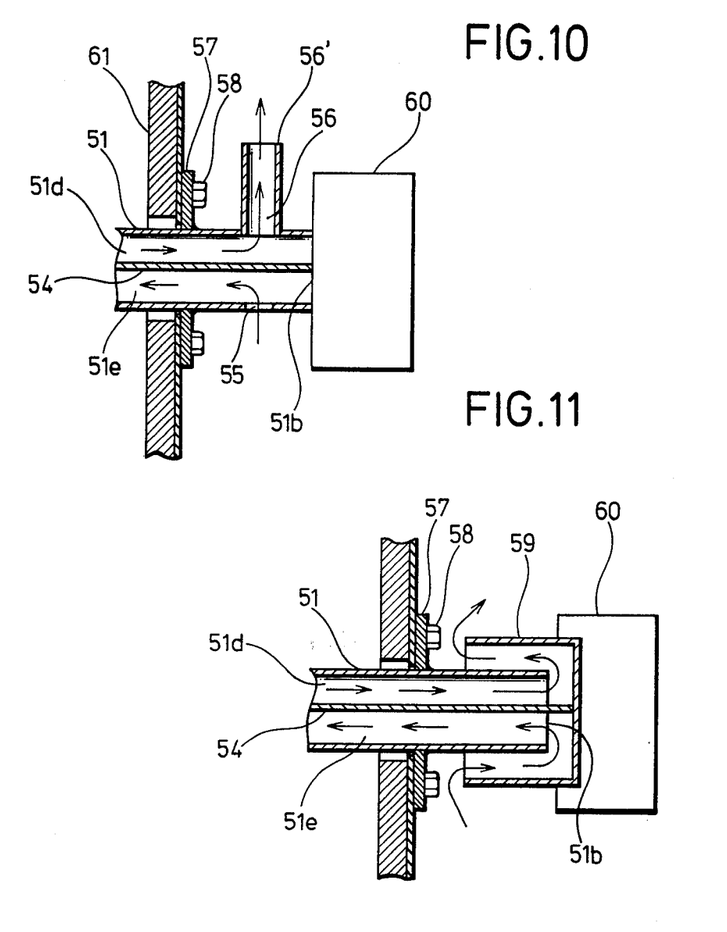
FIG. 10 depicts a partial elevational cross sectional view of a further illustrative embodiment of the invention.
FIG. 11 depicts a partial elevational cross sectional view of a still further illustrative embodiment.

The embodiments heretofore described are not exclusive. For example, it is possible to employ communication means as shown in FIGS. 10 and 11. In the embodiment shown in FIG. 10, probe 51 is provided with a discharge sleeve 56' connected to through hole 56 so that the convection in probe 51 is promoted by the chimney like action of discharge sleeve 56'. In contrast, in the embodiment shown in FIG. 11, probe 51 is devoid of through holes 55 and 56 shown in FIG. 7, but, instead, the passage of convection is formed through the gap between the bottom equipped cylindrical lid 59 and the portion 51b of the probe opposite the end.

As has been described, in the oxygen meter of this invention, the internal cavity of the probe is divided into two sections by a partition place and the air is introduced into the cavity divided into two sections, to eliminate the necessity for a pump for supplying air, or for a piping for introducing air for use of the measuring instrument, thereby to reduce the cost of production of the meter while remarkably improving the reliability of operation of same.

The foregoing description is illustrative of the principles of the invention. Numerous modifications and extensions thereof would be apparent to the workers skilled in the art. All such modifications and extensions thereof are to be considered to be within the spirit and scope of the invention.

What is claimed is:

1. A solid electrolyte type oxygen meter having a probe type detecting section including a solid electrolyte unit fixed to the end thereof so as to form a partition wall and adapted to produce a signal corresponding to the difference in the oxygen concentration between the inner side and outer side of said partition wall;

said oxygen meter comprising a contact portion secured to the inner wall surface of said probe near the end of the latter through an electrically insulating member; a test tube type solid electrolyte unit inserted into and affixed to said end of said probe, a first electrode and a second electrode closely secured to the outer wall surface and the inner wall surface of the closed end wall of said solid electrolyte unit, or the portion of said solid electrolyte unit near said end wall, a first lead closely attached to said outer wall surface of said solid electrolyte unit and providing a connection between said first electrode and said contact portion, and a second lead closely attached to said inner wall surface of said solid electrolyte unit and providing an electrical connection between said second electrode and the open end surface of said solid electrolyte unit; and a first conductor and a second conductor connected to said contact portion and said open end of said solid electrolyte unit, respectively, thereby to transmit the signals produced by said first and second electrodes.

2. The meter of claim 1, wherein said contact portion includes a contact ring provided with a recessed inner peripheral surface and affixed to the inner surface of said probe by an insulating adhesive, and a coil contact fitted in the recess of said contact ring.

3. The meter of claim 1, wherein said first and second leads are conductors which are formed on the wall surfaces of said electrolyte unit by baking of a platinum paste.

4. The meter of claim 1, wherein said first conductor is a wire lead disposed in said probe and covered by an insulator.

5. The meter of claim 1, wherein said second conductor includes a metallic mesh filter provided on the open end of said solid electrolyte unit, a flange for pressing said filter onto said open end and to affix said solid electrolyte unit to said probe and wherein the body of said probe is electrically conductive.

6. An oxygen meter of solid electrolyte type having a probe and a solid electrolyte secured to the end of said probe or a portion of said probe near said end so as to form a partition wall, so as to provide a signal corresponding to the difference in oxygen concentration between the inner side and the outer side of probe across said partition wall;

said oxygen meter comprising a cell unit comprising a conduit having one end located near said end of said probe and the other end projected into the portion of said probe opposite to said end, a solid electrolyte unit of test tube shape, and a flange integral with said solid electrolyte unit, said solid electrolyte unit being inserted into the end of said probe with the closed end of said solid electrolyte unit directed inwardly; a substantially U-shaped conduit having one end within the internal cavity of said solid electrolyte unit and the other end connected to a portion of said conduit near said end of said conduit, and a flange supporting said U-shaped conduit and jointed to said flange of said cell unit, and adapted to affix said cell unit to the end of said probe by means of a fixing tool.

* * * * *